(12) United States Patent
Wardlaw

(10) Patent No.: US 9,322,835 B2
(45) Date of Patent: Apr. 26, 2016

(54) METHOD AND APPARATUS FOR SELECTIVELY ADMIXING REAGENTS IN A SUBSTANTIALLY UNDILUTED BIOLOGIC FLUID SAMPLE ANALYSIS

(75) Inventor: Stephen C. Wardlaw, Lyme, CT (US)

(73) Assignee: Abbott Point of Care, Inc., Princeton, NJ (US)

( * ) Notice: Subject to any disclaimer, the term of this patent is extended or adjusted under 35 U.S.C. 154(b) by 1117 days.

(21) Appl. No.: 13/077,251

(22) Filed: Mar. 31, 2011

(65) Prior Publication Data

US 2011/0244593 A1 Oct. 6, 2011

Related U.S. Application Data

(60) Provisional application No. 61/319,331, filed on Mar. 31, 2010.

(51) Int. Cl.
| | |
|---|---|
| *G01N 1/10* | (2006.01) |
| *G01N 31/00* | (2006.01) |
| *G01N 35/02* | (2006.01) |
| *G01N 1/14* | (2006.01) |
| *G01N 35/00* | (2006.01) |

(52) U.S. Cl.
CPC ............ *G01N 35/025* (2013.01); *G01N 35/026* (2013.01); *G01N 1/14* (2013.01); *G01N 35/00584* (2013.01); *Y10T 436/2575* (2015.01)

(58) Field of Classification Search
CPC ..... G01N 1/14; G01N 35/026; G01N 35/025; G01N 35/00584; G01N 35/1002; G01N 35/1009; G01N 35/1016
See application file for complete search history.

(56) References Cited

U.S. PATENT DOCUMENTS

| | | | | |
|---|---|---|---|---|
| 4,066,412 | A * | 1/1978 | Johnson et al. | ................ 422/65 |
| 5,413,732 | A * | 5/1995 | Buhl et al. | ............. 252/182.11 |
| 6,723,290 | B1 * | 4/2004 | Wardlaw | ....................... 422/559 |
| 6,866,823 | B2 | 3/2005 | Levine et al. | |
| 7,850,916 | B2 | 12/2010 | Wardlaw | |
| 7,903,241 | B2 | 3/2011 | Wardlaw et al. | |
| 2004/0197233 | A1 | 10/2004 | Nagaoka | |

(Continued)

FOREIGN PATENT DOCUMENTS

| | | |
|---|---|---|
| EP | 2322939 | 9/2011 |
| WO | 0111374 | 2/2001 |

OTHER PUBLICATIONS

International Search Report for PCT/US11/30732, Aug. 18, 2011.

*Primary Examiner* — Christopher A Hixson
(74) *Attorney, Agent, or Firm* — O'Shea Getz P.C.

(57) ABSTRACT

A biologic fluid sample analysis method and system is provided that includes a reagent depository, and analysis chamber, a biologic fluid transfer system, and a programmable analyzer. The reagent depository has a plurality of reagent deposits, and each reagent deposit located at a position within the depository independent of the other reagent deposits. The analysis chamber is adapted to quiescently hold a biologic fluid sample and one or more reagents during analysis. The biologic fluid transfer system has at least one fluid transfer device. The programmable analyzer is adapted to control the biologic fluid transfer system to acquire a volume of sample from a sample reservoir, dispense a volume of the sample into the reagent depository, acquire a volume of sample and reagent from the reagent depository, and to transfer the sample and reagent to the analysis chamber, and to analyze the combined sample and reagent.

7 Claims, 3 Drawing Sheets

(56) References Cited

U.S. PATENT DOCUMENTS

2007/0243117 A1* 10/2007 Wardlaw ...................... 422/255
2009/0088336 A1    4/2009 Burd et al.
2009/0155123 A1    6/2009 Williams et al.
2010/0255605 A1   10/2010 Wardlaw
2011/0042582 A1    2/2011 Ingber et al.

* cited by examiner

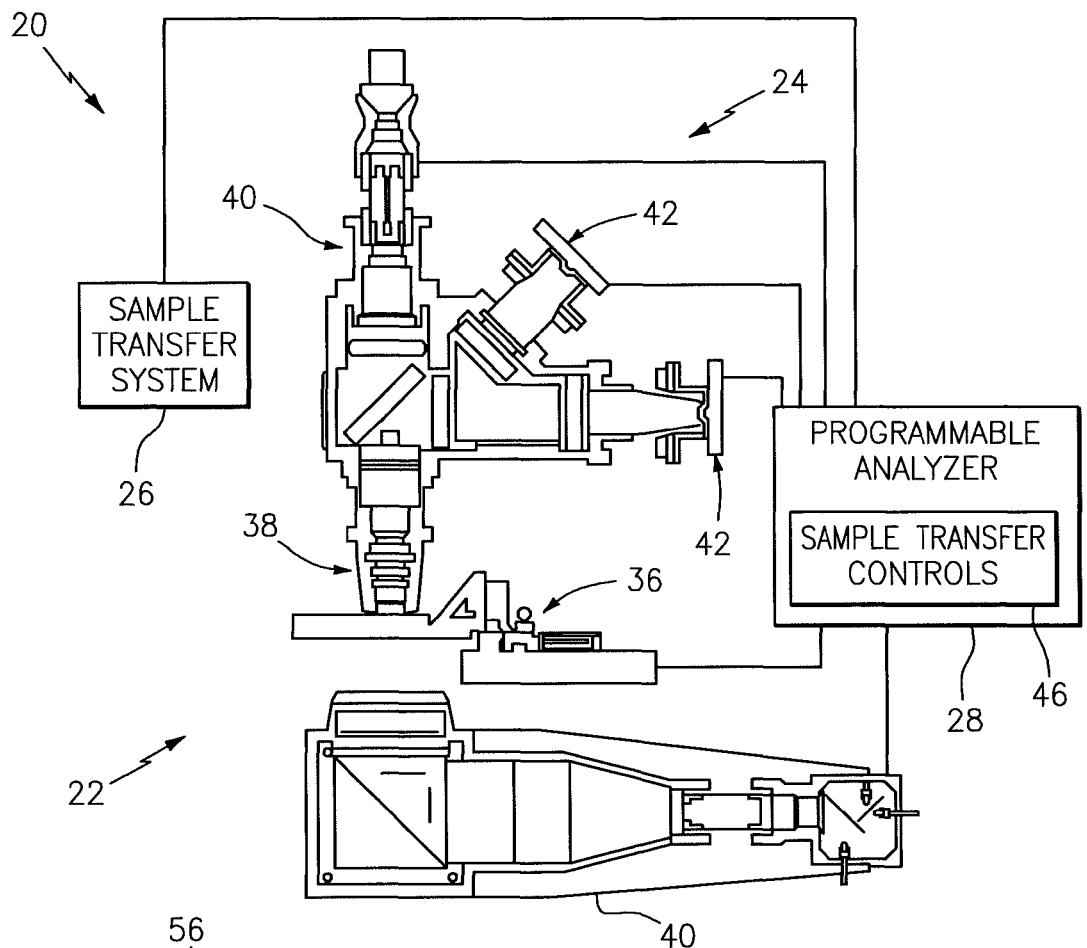
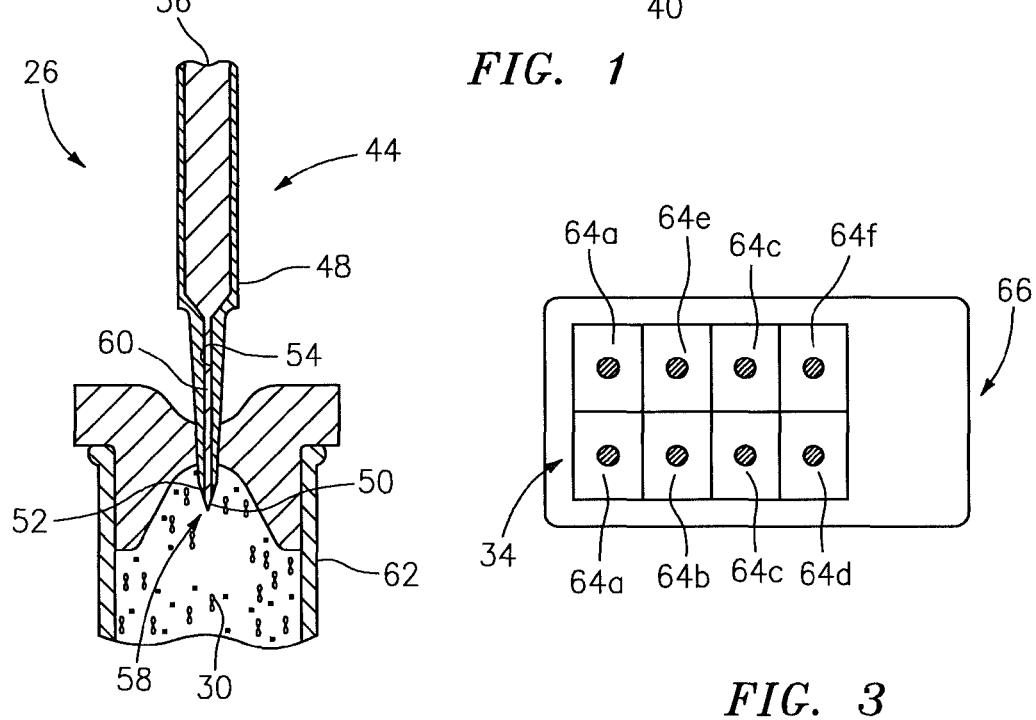
FIG. 1
FIG. 2
FIG. 3

METHOD AND APPARATUS FOR SELECTIVELY ADMIXING REAGENTS IN A SUBSTANTIALLY UNDILUTED BIOLOGIC FLUID SAMPLE ANALYSIS

The present application is entitled to the benefit of and incorporates by reference essential subject matter disclosed in U.S. Provisional Patent Application Ser. No. 61/319,331, filed Mar. 31, 2010.

BACKGROUND OF THE INVENTION

1. Technical Field

The present invention relates to methods and apparatuses for biologic fluid sample analyses in general, and to those that selectively admix one or more reagents with a biologic fluid sample in particular.

2. Background Information

Biologic fluid sample (e.g., whole blood, urine, cerebrospinal fluid, body cavity fluids, etc.) analyses often require the addition of one or more reagents to the sample prior to the analysis. Analyses of substantially undiluted whole blood, for example, often include an amount of a reagent (e.g., a colorant) that facilitates constituent identification. The phrase "substantially undiluted" as used herein describes a sample which is either not diluted at all or has not been diluted purposefully, but has had some reagents added thereto for purposes of the analysis. To the extent the addition of the reagents dilutes the sample, if at all, such dilution has no clinically significant impact on the analysis performed.

There is considerable advantage for biologic fluid sample analysis systems and sample cartridges to have flexibility to perform multiple tests, including tests that utilize different reagents. For example, a first analysis may require the addition of a first reagent to a particular sample to enable a first analysis, and the addition of a second reagent to the same sample to enable a second analysis.

What is needed, therefore, is an apparatus and a method that is adapted to provide a plurality of reagents in small amounts that are easily handled and that can be selectively added to and mixed with sample prior to analysis thereof.

DISCLOSURE OF THE INVENTION

According to an aspect of the present invention, a biologic fluid sample analysis system is provided that includes a reagent depository, and analysis chamber, a biologic fluid transfer system, and a programmable analyzer. The reagent depository has a plurality of reagent deposits, and each reagent deposit is located at a position within the depository independent of the other reagent deposits. The analysis chamber is adapted to quiescently hold a biologic fluid sample and one or more reagents during analysis. The biologic fluid transfer system has at least one fluid transfer device. The programmable analyzer is adapted to control the biologic fluid transfer system to acquire a volume of sample from a sample reservoir, dispense a volume of the sample into the reagent depository, acquire a volume of sample and reagent from the reagent depository, and to transfer the sample and reagent to the analysis chamber, and to analyze combined sample and reagent.

According to another aspect of the present invention, a method of handling a biologic fluid sample for analysis is provided. The method includes the steps of: a) providing a reagent depository having a plurality of reagent deposits, each reagent deposit located within the depository at a position independent of the other reagent deposits; b) acquiring a volume of sample from a sample reservoir using a biologic fluid transfer system, having at least one fluid transfer device; c) dispensing a volume of the acquired sample into the reagent depository from the fluid transfer device; d) acquiring a volume of sample and reagent from the reagent depository using the fluid transfer device; and e) transferring the sample and reagent to an analysis chamber for analysis, using the fluid transfer device.

The present apparatus and method, and advantages associated therewith, will become more readily apparent in view of the detailed description provided below, including the accompanying drawings.

BRIEF DESCRIPTION OF THE DRAWINGS

FIG. 1 is a schematic view of the present biologic fluid sample analysis system.

FIG. 2 is a diagrammatic representation of a biologic fluid transfer device portion of a sample transfer system engaged with a sample collection vessel.

FIG. 3 is a diagrammatic view of a card that has a reagent depository disposed on a surface.

DETAILED DESCRIPTION

Figure 4:
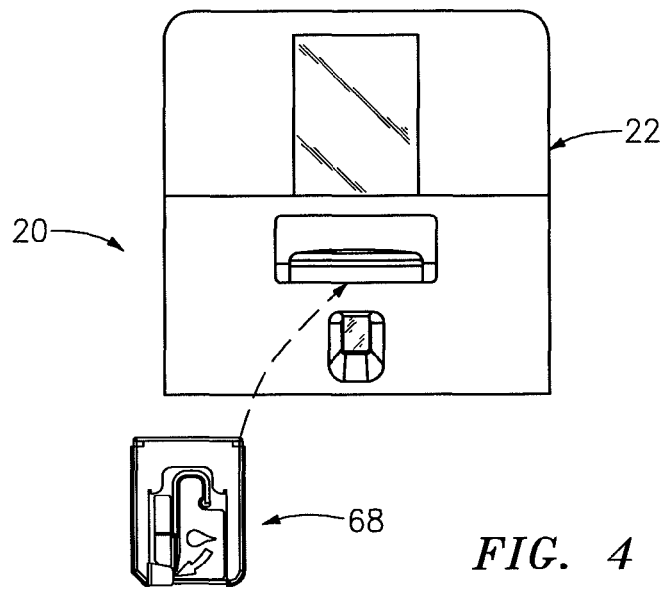
FIG. 4 is a diagrammatic view of an embodiment of a present analysis system adapted to receive an analysis cartridge.

Referring to FIGS. 1-3, the present biologic fluid sample analysis system 20 is diagrammatically shown that includes an automated analysis device 22 that includes imaging hardware 24, a sample transfer system 26, and programmable analyzer 28. The analysis device 22 is adapted to image a biologic fluid sample 30 (e.g., see FIG. 2) quiescently residing within an analysis chamber 32. A reagent depository 34 is included, and is typically disposed on a substrate (e.g., a reagent card, an analysis cartridge, etc.) that can be received and accessed by the analysis device 22.

The imaging hardware 24 includes a cartridge holding and manipulating device 36, a sample objective lens 38, a plurality of sample illuminators 40, and an image dissector 42. One or both of the objective lens 38 and cartridge holding device 36 are movable toward and away from each other to change a relative focal position. The sample illuminators 40 illuminate the sample using light along predetermined wavelengths. Light transmitted through the sample, or fluoresced from the sample, is captured using the image dissector 42, and a signal representative of the captured light is sent to the programmable analyzer 28, where it is processed into an image. The imaging hardware described in U.S. Pat. No. 6,866,823 and U.S. Patent Application No. 61/371,020 (each of which is hereby incorporated by reference in its entirety) are acceptable types of imaging hardware for the present analysis device 22. The present invention is not limited to use with the aforesaid imaging hardware, however.

The sample transfer system 26 includes one or more biologic fluid transfer devices 44 (e.g., see FIG. 2), apparatus (e.g., electromechanical actuators and structure) operable to move the transfer device(s), and controls 46 (shown diagrammatically incorporated into programmable analyzer 28) adapted to control the operation and movement of the transfer device(s) 44. The transfer device 44 is operable to acquire and dispense small volumes of sample 30, and sample and reagent(s) combined. As will be described below, the programmable analyzer 28 can be adapted to provide the controls 46 required for the sample transfer system 26.

Referring to FIG. 2, an example of an acceptable fluid transfer device 44 is described in U.S. patent application Ser. No. 12/417,399 (hereinafter "the '399 application"), filed Apr. 2, 2009, which is hereby incorporated by reference in its entirety. Briefly stated, the aforesaid transfer device 44 includes an outer casing 48 and a lance 50. The outer casing 48 has a tip 52 with a bore 54 extending lengthwise through the tip 52, which bore 54 has a constant cross-sectional geometry. The lance 50 has a length extending between an operating end 56 and a sample end 58, including a seal segment 60 contiguous with the sample end 58. The seal segment 60 of the lance 50 forms an interference fit with the outer casing bore 54, which interference fit is operable to create a seal between the seal segment 60 and the bore 54. The transfer device 44 is selectively disposable in an empty volume position and a plurality of sample volume positions (each associated with a different sample volume) by relative lengthwise movement between the outer casing 48 and the lance 50. The amount of linear movement of the lance 50 can be equated to sample volume; e.g., "x" ml of sample 30 acquired per mm of lance 50 travel relative to the outer casing 48. In the empty volume position, the sample end 58 extends at least flush with the tip exterior surface. In each sample volume position, the sample end 58 of the lance 50 is disposed within the bore 54 a distance away from the aperture. The sample transfer system 26 is not limited to the fluid transfer device 44 described in the '399 application, however. A pipette is an example of an alternative type of transfer device that can be used within the present system 26.

Figure 6:
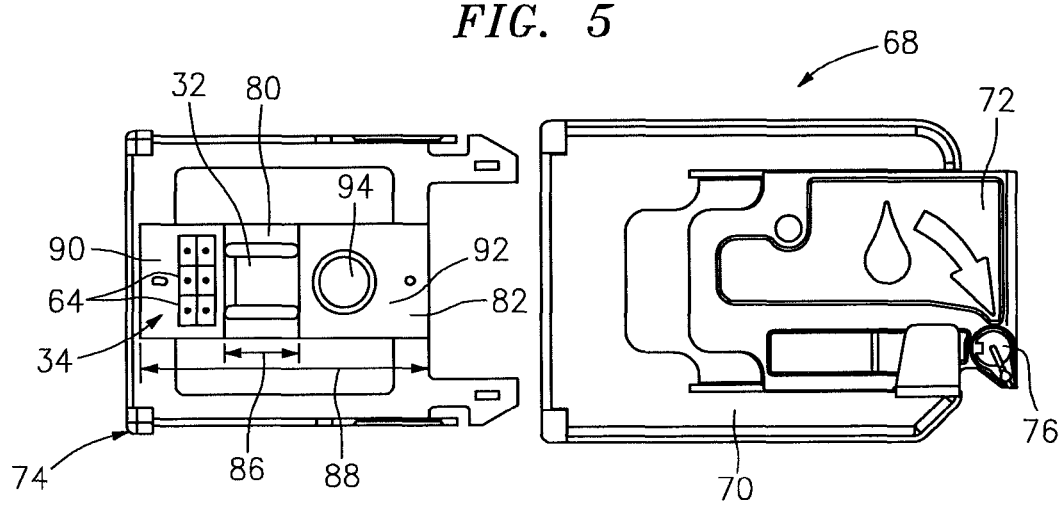
FIG. 6 is an exploded view of the cartridge embodiment shown in FIG. 5, with the fluid module open and the imaging tray disposed outside of the housing.

The sample transfer system 26 is adapted to acquire a sample volume using the fluid transfer device 44 from a body of sample 30 residing within a sample collection vessel 62, an analysis chamber 32 (e.g., see FIGS. 6 and 7), or other reservoir, and from a reagent depository 34 (e.g., see FIGS. 3 and 6). An example of a sample collection vessel 62 is a Vacutainer® type biologic sample container available from Becton, Dickinson and Company, New Jersey, USA. The sample transfer system 26 is further adapted to dispense a small, known volume of sample 30 from the fluid transfer device 44 to a predetermined location in the reagent depository 34, and separately into an analysis chamber 32.

Referring to FIG. 1, the programmable analyzer 28 includes a central processing unit (CPU) and is in communication with the imaging hardware 24 and the sample transfer system 26. The CPU is adapted (e.g., programmed) to receive the signals and selectively perform the functions necessary to operate the imaging hardware 24 and the transfer system 26. The programmable analyzer 28 is further adapted to perform analysis on collected sample images and provide results of such analyses to an end user. U.S. Pat. No. 7,903,241 (hereinafter "the '241 patent"), which is hereby incorporated by reference in its entirety, includes a programmable analyzer 28 adapted to perform analyses on a biologic fluid sample 30. The '241 patent is detailed here as an example of an analysis device having a programmable analyzer 28. The present invention is not, however, limited to performing the analyses disclosed in the '241 patent.

The present programmable analyzer 28 is further adapted to operate the fluid transfer device(s) 44 (see FIG. 2) to acquire a volume sample 30 from a source (e.g., a reservoir) and dispense an amount of sample 30. The sample 30 may be dispensed within an analysis chamber 32 (or at a position where it can travel into a chamber 32) or within the reagent depository 34, where the dispensed amount of sample 30 can hydrate and mix with one or more reagents. For those instances where sample 30 is dispensed within the reagent depository 34, the programmable analyzer 28 is further adapted to subsequently acquire a volume of the sample 30 and reagent, and then dispense a volume of the sample 30 and reagent at a second position within the reagent depository 34 for mixing with a second reagent, or at a position in an analysis chamber 32, or at a position where the sample 30 and reagent can travel into an analysis chamber 32. The process of acquiring a volume of sample 30 and reagent and subsequent dispensing of the sample 30 and reagent provides some amount of mixing of the reagent within the sample 30 volume. The present analysis system 20 may utilize more than one programmable analyzer 28 to perform the above described functions. It should be noted that the functionality of the programmable analyzer(s) 28 may be implemented using hardware, software, firmware, or a combination thereof. A person skilled in the art would be able to program the unit to perform the functionality described herein without undue experimentation.

Figure 9:
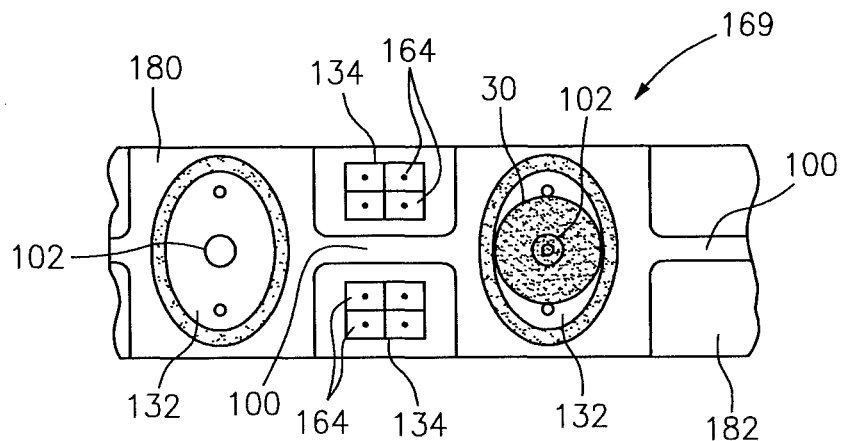
FIG. 9 illustrates an embodiment of the planar members shown in FIG. 8.

Referring to FIGS. 3, 6, and 9, the reagent depository 34 includes a plurality of reagent deposits 64 (referred to as "reagent dots 64"). For purposes of the present invention, the term "reagent" is defined as including any substance that can be added to the biologic fluid sample 30 and has utility for the analysis at hand. Acceptable reagents include, but are not limited to, colorants (e.g., Acridine Orange, Astrozone orange, etc.), isovolumetric sphering agents (e.g., a zwitterionic detergent), lysing agents, etc. In a preferred embodiment, the reagent dots 64 are in at least partially dehydrated form that can be at least partially hydrated by the addition of biologic fluid sample 30. The dehydrated reagent form facilitates handling and is readily stored. The present invention is not limited to a dehydrated reagent form, however. The reagent dots 64 within a reagent depository 34 may all be different types of reagents or may include more than one reagent dot 64 of a particular type of reagent. FIG. 3, for example, illustrates a reagent depository 34 having six different types of reagents (i.e., 64a-64f), and also has multiple reagent dots 64 of the same type (i.e., two "64a" and two "64c" reagent dots).

The reagent depository 34 can be located on any surface that can be accessed by the sample transfer system 26 and associated biologic fluid transfer device(s) 44, and which surface is configured to permit sample 30 to be deposited on one or more reagent dots 64 within the depository 34 and subsequently reacquired by the sample transfer system 26. The reagent depository 34 is configured such that a volume of sample 30 can be deposited on a particular reagent dot 64 without interference from adjacent reagent dots 64 within the depository 34. As a result, the sample volume 30 dispensed and subsequently reacquired is subjected to only the intended reagent dot 64, without contamination from adjacent reagent dots 64.

As indicated above, the reagent depository 34 may be disposed on a substrate (e.g., a reagent card 66, an analysis cartridge 68, 168, etc.) that can be received and accessed by the analysis device 22. For example, in a first embodiment, the reagent depository 34 can be disposed on a card 66 (see FIG. 3) that is independent of an analysis chamber 32 (e.g., see FIG. 6), and which can be received and accessed by the analysis device 22. Once received by the analysis device 22, the reagent card 66 can be accessed by the sample transfer system 26.

Figure 5:
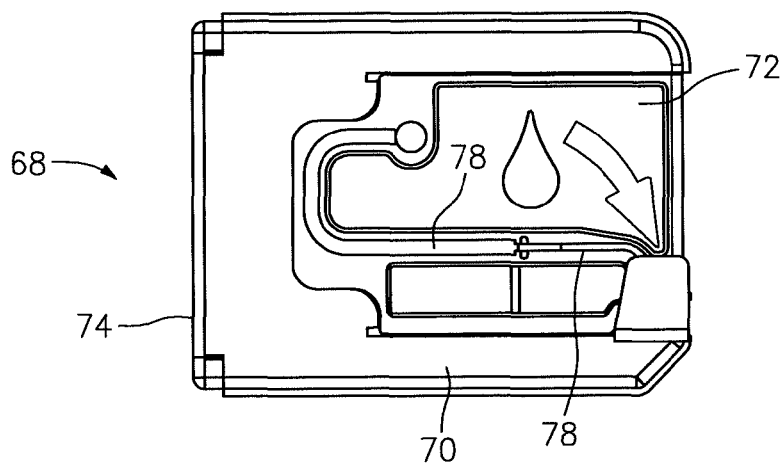
FIG. 5 is a diagrammatic planar view of a cartridge embodiment.
Figure 7:
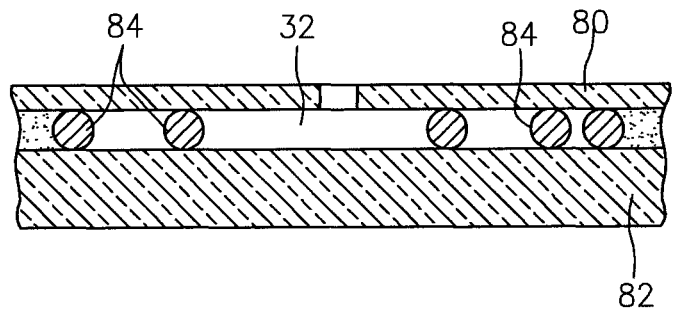
FIG. 7 is a diagrammatic cross-sectional view of an analysis chamber.

Referring to FIGS. 4-7, in a second embodiment the reagent depository 34 may be included in a disposable cartridge 68 that is adapted for use with the analysis system 20. Examples of such cartridges 68 are disclosed in U.S. patent application Ser. No. 12/971,860 (hereinafter "the '860 application") and 61/428,659, both of which applications are hereby incorporated by reference in their entirety. The cartridge 68 described in the '860 application, for example, includes a housing 70, a fluid module 72, and an imaging tray 74. FIG. 5 illustrates the cartridge 68 with the fluid module 72 closed and the imaging tray 74 disposed within the housing 70. FIG. 6 is an exploded view of the cartridge 68, illustrating the fluid module 72 open and the imaging tray 74 outside of the housing 70. The fluid module 72 includes a sample acquisition port 76 and a plurality of internal channels 78 (see FIG. 5). The imaging tray 74, which can be slid outside of the housing 70 for access, includes an analysis chamber 32 having an upper panel 80 and a lower panel 82 which are spaced apart from one another and are configured to receive a fluid sample 30 there between for image analysis. A diagrammatic cross-sectional view of an analysis chamber 32 is shown in FIG. 7, illustrating the upper panel 80 and lower panel 82 separated from one another by separator beads 84. At least one of the panels 82, 84 is transparent. As can be seen in the embodiment shown in FIG. 6, the upper panel 80 has a width that is substantially equal to the width of the lower panel 82. The length 86 of the upper panel 80 is less than the length 88 of the lower panel 82, thereby exposing a first portion 90 and a second portion 92 of the upper surface of the lower panel 82, which portions 90, 92 are disposed on opposite sides of the upper panel 80. Sample introduced into the acquisition port 76 can travel through the internal channels 78 and pass onto the imaging tray 74.

In an embodiment of the cartridge 68 having utility within the present invention, a reservoir 94 is formed on the second portion 92 of the upper surface of the lower panel 82, adjacent an open edge of the analysis chamber 32. The perimeter of the reservoir 94 may be formed, for example, by a hydrophobic coating or by a glue bead. The reagent depository 34 is disposed on the first portion 90 of the upper surface of the lower panel 82, with a plurality of reagent dots 64 separated from one another.

Figure 8:
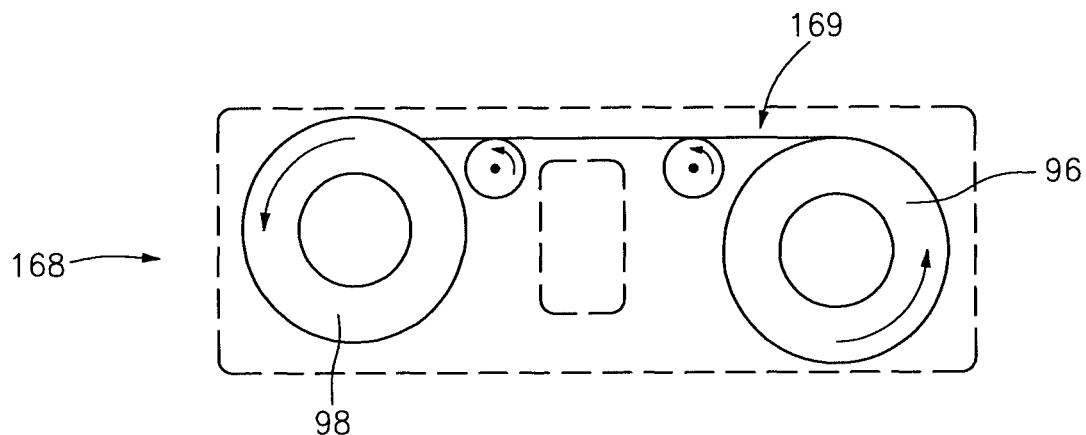
FIG. 8 is a diagrammatic view of another cartridge embodiment, which embodiment includes cartridge planar members transferable between a source reel and a take-up reel.

Now referring to FIGS. 8 and 9, in an alternative embodiment, the analysis system 20 (see FIG. 1) may be operable with an analysis cartridge 168 having a tape 169, formed by an upper panel 180 and a lower panel 182, in a reeled assembly. The upper panel 180 and the lower panel 182 are separated from one another by a predetermined distance for receiving sample there between; e.g., in the manner shown in FIG. 7. The panels 180, 182 are initially stored on a source reel 96 and are unwound to allow analysis of the sample, after which analysis the panels 180, 182 are wound up onto a take-up reel 98. U.S. Pat. No. 7,850,916, which is hereby incorporated by reference in its entirety, describes such a cartridge. According to the present invention, the upper panel 180 of the tape 169 includes necked portions 100 disposed between analysis chambers 132, wherein the upper surface of the lower panel 182 is exposed. The upper panel 180 also includes a sample port 102 that allows sample 30 to be deposited within the analysis chamber 132. The perimeter of the analysis chambers 132 are defined by a glue bead. FIG. 9 illustrates an analysis chamber 132 without sample 30, and an analysis chamber 132 with sample 30. The reagent depository 134 is disposed on the exposed portions of the upper surface of the lower panel 182, with a plurality of reagent dots 164 separated from one another.

These two cartridge embodiments are provided to illustrate how the present invention reagent depository 34 can be used with different types of cartridges. The present system is not limited to any particular cartridge embodiment.

Operation:

Referring to FIGS. 1-7, prior to analysis of the biologic fluid sample 30 (e.g., whole blood) within the analysis system 20, the sample transfer system 26 is operated to acquire a volume of biologic fluid sample 30 and to subsequently dispense a volume of the sample 30 using the fluid transfer device 44. In some applications, the fluid transfer device 44 may dispense a volume of the sample directly into an analysis chamber 32 (or a portion of the analysis chamber 32) to create an "unmixed" or "standard" sample for the purpose of comparison. In other applications, the fluid transfer device 44 may dispense a volume of the sample 30 into the reagent depository 34 at a position aligned with a reagent dot 64. The volume of sample dispensed in the reagent depository 34 is adequate to hydrate an amount of the reagent dot 64, which amount is sufficient for the analysis at hand. Once adequate hydration of the reagent dot 64 has occurred and the sufficient amount of reagent has migrated into the sample volume, the fluid transfer device 44 is operated to re-acquire the sample, now including the reagent. During the re-acquisition process, the reagent and sample mix to some degree. A volume of the sample and reagent mix may then be dispensed on another reagent dot 64 for acquisition of a second reagent, or may be dispensed relative to the analysis chamber 32 for analysis within the chamber 32.

Using the analysis cartridge 68 shown in FIGS. 4-6 as an example, the sample transfer system 26 may be operated to acquire a volume of biologic fluid sample 30 from a reservoir 94 disposed on the upper surface of the lower panel 82 (see FIG. 6), and to subsequently dispense a volume of the sample 30 directly into an analysis chamber 32 or into the reagent depository 34 at a position aligned with a reagent dot 64. If the sample 30 is dispensed on a reagent dot 64, an amount of the reagent dot 64 is hydrated and mixed with the sample 30. The fluid transfer device 44 is subsequently operated to re-acquire the sample, now including the reagent. The volume of mixed sample and reagent may then be dispensed on another reagent dot 64 for acquisition of a second reagent, or may be dispensed relative to the analysis chamber 32 for analysis within the chamber 32.

Now using the analysis cartridge shown in FIGS. 8 and 9 as an example, the sample transfer system 26 may be operated to acquire a volume of biologic fluid sample 30 from a collection vessel 62 (e.g., see FIG. 2), such as a Vacutainer®, loaded into the analysis system 20, where it can be accessed by the fluid transfer device 44 of the sample transfer system 26. The sample transfer system 26 subsequently dispenses a volume of the sample 30 directly into an analysis chamber 132, or into the reagent depository 134 at a position aligned with a reagent dot 164. If the sample 30 is dispensed on a reagent dot 164, an amount of the reagent dot 164 is hydrated and mixed with the sample 30. The fluid transfer device 44 is subsequently operated to re-acquire the sample, now including the reagent. The volume of mixed sample and reagent may then be dispensed on another reagent dot 164 for acquisition of a second reagent, or may be dispensed into the analysis chamber 132 via the sample port 102 for analysis within the chamber 132.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. A biologic fluid sample analysis system, comprising:
    a disposable cartridge that includes a reagent depository having a plurality of reagent deposits, each reagent deposit located at a position within the depository independent of the other reagent deposits, and an analysis chamber having an upper panel and a lower panel spaced apart from one another, which analysis chamber is configured to quiescently hold a sample-reagent mixture for imaging of the mixture quiescently residing between the panels;
    a biologic fluid transfer system having at least one fluid transfer device, which fluid transfer device includes a body with an interior cavity and which fluid transfer device is operable to selectively draw fluid into the interior cavity and expel fluid from the interior cavity; and
    a programmable analyzer adapted to control the biologic fluid transfer system to acquire a volume of sample from a sample reservoir, dispense the acquired sample volume into the reagent depository to mix with at least one of the reagent deposits and thereby produce the sample-reagent mixture, acquire a volume of the sample-reagent mixture from the reagent depository, transfer the sample-reagent mixture to the analysis chamber, image the sample-reagent mixture quiescently residing within the analysis chamber, and analyze the biologic fluid sample using one or more images of the sample-reagent mixture.

2. The analysis system of claim 1, wherein the programmable analyzer is further adapted to control the biologic fluid transfer system to acquire a second volume of sample from the sample reservoir, dispense at least a portion of the second volume into the reagent depository, acquire a volume of a second sample-reagent mixture from the reagent depository, and to transfer the second sample-reagent mixture to the analysis chamber.

3. The analysis system of claim 1, wherein the plurality of reagent deposits include one or more colorants capable of staining or otherwise distinguishing constituents within the biologic fluid sample.

4. The analysis system of claim 1, wherein the reservoir is a sample collection vessel.

5. The analysis system of claim 1, wherein the fluid transfer device includes a lance at least partially received within an outer casing.

6. The analysis system of claim 1, wherein the fluid transfer device includes a pipette.

7. A method for analyzing a biologic fluid sample, comprising:
    providing a disposable cartridge that includes a reagent depository having a plurality of reagent deposits, each reagent deposit located at a position within the depository independent of the other reagent deposits, and an analysis chamber having an upper panel and a lower panel spaced apart from one another, which analysis chamber is configured to quiescently hold a sample-reagent mixture for imaging of the mixture quiescently residing between the panels;
    providing a biologic fluid transfer system having at least one fluid transfer device, which fluid transfer device includes a body with an interior cavity and which fluid transfer device is operable to selectively draw fluid into the interior cavity and expel fluid from the interior cavity;
    providing a programmable analyzer;
    acquiring a volume of sample from a sample reservoir using the biologic fluid transfer system, which transfer system is controlled by the programmable analyzer;
    dispensing the acquired sample volume into the cartridge reagent depository to mix with at least one of the reagent deposits and thereby produce the sample-reagent mixture;
    acquiring a volume of the sample-reagent mixture from the cartridge reagent depository;
    transferring the sample-reagent mixture to the analysis chamber;
    imaging the sample-reagent mixture quiescently residing within the analysis chamber to produce one or more images of the sample-reagent mixture; and
    analyzing the biologic fluid sample using the one or more images of the sample-reagent mixture.

* * * * *